(12) United States Patent
Yao et al.

(10) Patent No.: US 9,315,636 B2
(45) Date of Patent: Apr. 19, 2016

(54) STABLE METAL COMPOUNDS, THEIR COMPOSITIONS AND METHODS

(71) Applicants: Huirong Yao, Plainsboro, NJ (US); M. Dalil Rahman, Flemington, NJ (US); Salem K. Mullen, Florham Park, NJ (US); JoonYeon Cho, Bridgewater, NJ (US); Clement Anyadiegwu, Parlin, NJ (US); Munirathna Padmanaban, Bridgewater, NJ (US)

(72) Inventors: Huirong Yao, Plainsboro, NJ (US); M. Dalil Rahman, Flemington, NJ (US); Salem K. Mullen, Florham Park, NJ (US); JoonYeon Cho, Bridgewater, NJ (US); Clement Anyadiegwu, Parlin, NJ (US); Munirathna Padmanaban, Bridgewater, NJ (US)

(73) Assignee: AZ ELECTRONIC MATERIALS (LUXEMBOURG) S.A.R.L., Luxembourg (LU)

( * ) Notice: Subject to any disclaimer, the term of this patent is extended or adjusted under 35 U.S.C. 154(b) by 382 days.

(21) Appl. No.: 13/707,993

(22) Filed: Dec. 7, 2012

(65) Prior Publication Data

US 2014/0159278 A1    Jun. 12, 2014

(51) Int. Cl.
| | |
|---|---|
| C07F 7/00 | (2006.01) |
| C08K 5/00 | (2006.01) |
| C08G 79/00 | (2006.01) |
| C07F 7/28 | (2006.01) |
| G03F 7/09 | (2006.01) |
| G03F 7/004 | (2006.01) |
| G03F 7/075 | (2006.01) |

(52) U.S. Cl.
CPC . *C08G 79/00* (2013.01); *C07F 7/28* (2013.01); *G03F 7/091* (2013.01); *G03F 7/0043* (2013.01); *G03F 7/075* (2013.01)

(58) Field of Classification Search
CPC ............ C08G 79/00; C07F 7/28; G03F 7/091
USPC ........ 264/212; 556/55; 524/397; 106/287.24, 106/287.13, 287.19
See application file for complete search history.

(56) References Cited

U.S. PATENT DOCUMENTS

| | | | |
|---|---|---|---|
| 3,474,054 A | 10/1969 | White | |
| 4,200,729 A | 4/1980 | Calbo | |
| 4,251,665 A | 2/1981 | Calbo | |
| 4,491,628 A | 1/1985 | Ito et al. | |
| 5,178,989 A | 1/1993 | Heller et al. | |
| 5,187,019 A | 2/1993 | Calbo et al. | |
| 5,350,660 A | 9/1994 | Urano et al. | |
| 5,772,978 A | 6/1998 | Bailey et al. | |
| 5,843,624 A | 12/1998 | Houlihan et al. | |
| 5,879,859 A | 3/1999 | Buchwalter et al. | |
| 6,242,156 B1 | 6/2001 | Teng | |
| 6,348,299 B1 | 2/2002 | Aviram et al. | |
| 6,447,980 B1 | 9/2002 | Rahman et al. | |
| 6,723,488 B2 | 4/2004 | Kudo et al. | |
| 6,790,587 B1 | 9/2004 | Feiring et al. | |
| 6,818,258 B2 | 11/2004 | Kaneko et al. | |
| 6,849,377 B2 | 2/2005 | Feiring et al. | |
| 6,866,984 B2 | 3/2005 | Jung et al. | |
| 6,916,590 B2 | 7/2005 | Kaneko et al. | |
| 7,416,834 B2 | 8/2008 | Abdallah et al. | |
| 7,727,902 B2 | 6/2010 | Takei et al. | |
| 7,767,368 B2 | 8/2010 | Fukushima et al. | |
| 7,803,458 B2 | 9/2010 | Flaim et al. | |
| 8,039,201 B2 | 10/2011 | Yao et al. | |
| 2003/0235786 A1 | 12/2003 | Krishnamurthy et al. | |
| 2004/0029041 A1 | 2/2004 | Shih et al. | |
| 2004/0058275 A1 | 3/2004 | Neef et al. | |
| 2004/0102048 A1 | 5/2004 | Yamaguchi | |
| 2004/0181031 A1 | 9/2004 | Nogi et al. | |
| 2004/0224616 A1 | 11/2004 | Shiho et al. | |
| 2005/0164133 A1 | 7/2005 | Rangarajan et al. | |
| 2006/0263708 A1 | 11/2006 | Wu et al. | |
| 2007/0015083 A1 | 1/2007 | Babich et al. | |
| 2007/0116640 A1 | 5/2007 | Kim et al. | |
| 2007/0224483 A1 | 9/2007 | Alberti et al. | |
| 2007/0243473 A1 | 10/2007 | Mizushima et al. | |
| 2008/0044764 A1 | 2/2008 | Takahashi et al. | |
| 2008/0076064 A1 | 3/2008 | Sun | |
| 2009/0239080 A1 | 9/2009 | Ito et al. | |
| 2009/0286188 A1 | 11/2009 | Hatakeyama et al. | |
| 2010/0028804 A1 | 2/2010 | Iwato et al. | |
| 2010/0099044 A1 | 4/2010 | Hatakeyama et al. | |
| 2010/0130697 A1 | 5/2010 | Katayama et al. | |
| 2011/0081615 A1 | 4/2011 | Kon | |
| 2011/0207864 A1 | 8/2011 | Nakamura et al. | |
| 2011/0213190 A1* | 9/2011 | Cazaux et al. ................. | 585/511 |
| 2012/0223418 A1 | 9/2012 | Stowers et al. | |
| 2012/0264039 A1 | 10/2012 | Ito et al. | |
| 2012/0288300 A1 | 11/2012 | Matsusaki et al. | |
| 2012/0328990 A1 | 12/2012 | Yao et al. | |
| 2013/0040140 A1 | 2/2013 | Joo et al. | |

(Continued)

FOREIGN PATENT DOCUMENTS

| | | | | |
|---|---|---|---|---|
| CH | WO 2011032837 A1 * | 3/2011 | .......... | B01J 31/0214 |
| EP | 1 798 599 A1 | 6/2007 | | |

(Continued)

OTHER PUBLICATIONS

U.S. Appl. No. 13/707,993—STIC STN Results—Aug. 3, 2015—Relevant refs not used in 102, 42 pages.*
Lubben, Timothy V.; Wolczanski, Peter T., Journal of the American Chemical Society (1987), 109(2), 424-35.*
Piggot, Patrice M. T.; Hall, Lincoln A.; White, Andrew J. P.; et al.., Inorg Chem (2004), 43(3), 1167-1174; Jia, Junhua; Blake, Alexander J.; Champness, Neil R., et al., Inorg Chem (2008), 47(19), 8652-8664; Zuniga, Maria Felisa; Kreutzer, Johannes; Teng, Weijie; Ruhlandt-Senge, Karin, Inorg Chem (2007), 46(24), 10400-10409.*

(Continued)

*Primary Examiner* — Porfirio Nazario Gonzalez
*Assistant Examiner* — Kofi Adzamli
(74) *Attorney, Agent, or Firm* — Mitchell Brustein (57) ABSTRACT

The present disclosure relates to soluble, multi-ligand-substituted metal compounds with improved stability as well as compositions made from them and methods of their use.

22 Claims, 5 Drawing Sheets

(56) References Cited

U.S. PATENT DOCUMENTS

| | | | |
|---|---|---|---|
| 2013/0123137 A1 | 5/2013 | Reichardt et al. |
| 2014/0000948 A1 | 1/2014 | Nagai et al. |
| 2014/0356792 A1 | 12/2014 | Noya |
| 2015/0004801 A1 | 1/2015 | Rahman et al. |
| 2015/0064904 A1 | 3/2015 | Yao et al. |

FOREIGN PATENT DOCUMENTS

| | | | |
|---|---|---|---|
| EP | 1 892 089 A1 | | 2/2008 |
| EP | 2 447 775 A1 | | 5/2012 |
| EP | 2 479 615 A1 | | 7/2012 |
| JP | 63-56529 A1 | | 3/1988 |
| JP | 3-138922 A | | 6/1991 |
| JP | 6-32756 A | | 2/1994 |
| JP | 2000-10293 A | | 1/2000 |
| JP | 2005-307101 A | | 11/2005 |
| JP | 2006-98284 A | | 4/2006 |
| JP | 2007-61720 A | | 3/2007 |
| WO | WO 2011032837 A1 | * | 3/2011 |

OTHER PUBLICATIONS

Tao, Ruoyuan; Miyamoto, Daisuke; Aoki, Takahiro; Fujinami, Tatsuo, Journal of Power Sources (2004), 135(1-2), 267-272.*

Notice of Allowance and Fee(s) Due notification date Jun. 24, 2015 for U.S. Appl. No. 14/237,720.

Restriction Requirement notification date May 11, 2015 for U.S. Appl. No. 14/015,222.

Office Action notification date Jul. 10, 2015 for U.S. Appl. No. 14/154,929.

International Search Report for PCT/JP2012/070426 date of mailing Sep. 4, 2012, which corresponds to U.S. Appl. No. 14/237,720.

D. Abdallah et al., "Image Reversal Trilayer Process Using Standard Positive Photoresist", SPIE vol. 7273, No. 72732K, pp. 72732K-1-pp. 72732K-9 (2009).

D. Bajuk-Bogdanovic, "A Study of 12-tungstosilicic acid and 12-molybdophosphoric acids in solution," Journal of the Serbian Chemical Society vol. 73(2), pp. 197-pp. 209 (2008).

H. Levy et al., "Structure of Silico-Tungstic acid in Aqueous solution", The Journal of Chemical Physics vol. 30 No. 6, pp. 1486-pp. (1959).

J. Meador et al., "193-nm Multilayer Imaging Systems", SPIE vol. 5039, pp. 948-pp. 959 (2003).

J. Meador et al., "New Materials for 193-nm Trilayer Imaging", SPIE vol. 5376, pp. 1136-pp. 1148 (2004).

S. Moon et al., Three-Component Photopolymers Based on Thermal Cross-Linking and Acidolytic De-Cross-Linking of Vinyl Ether Groups. Effects of Binder Polymers on Photopolymer Characterictics, Chem. Mater. vol. 6, pp. 1854-pp. 1880 (1994).

M. Pope et al., "Polyoxymetalate Chemistry: An Old Field with New Dimensions in Several Disciplines", Angew. Chem. Int. Ed. Engl. vol. 30, pp. 34-pp. 48 (1991).

H. Schacht et al., "Acid Labile Cross-Liked Units: A Concept for Improved Positive Deep-UV Photoresists", ACS Symp. Ser. 706, pp. 78-pp. 94 (1998).

A. Scroggie et al., "The Crystal Structure of Anhydrous Silicotungstic Acid and Related Compounds, and Their Probable Molecular Formulas," Proceedings of the National Academy of Sciences vol. 15, No. 1, pp. 1-pp. 8 (1929).

T. Yamaoka et al., "Reactions of vinyl ethers and application to photoreactive process", Trends in Photochemistry and. Photobiology vol. 7, pp. 45-pp. 70 (2001).

Notification of the First Office Action dated Sep. 1, 2014 from the Chinese Patent Office for CN2012800262639, which corresponds to U.S. Appl. No. 13/164,869.

English Translation of Notification of the First Office Action dated Sep. 1, 2014 from the Chinese Patent Office for CN2012800262639, which corresponds to U.S. Appl. No. 13/164,869.

Office Action notification date Mar. 11, 2015 for U.S. Appl. No. 14/237,720.

Form PCT/ISA/220, Form PCT/ISA/210, and Form PCT/ISA/237 dated Feb. 6, 2015 for PCT/EP2014/076919, which corresponds to U.S. Appl. No. 14/015,222.

Form PCT/ISA/220, Form PCT/ISA/210, and Form PCT/ISA/237 dated Nov. 28, 2014 for PCT/EP2014/067749, which corresponds to U.S. Appl. No. 14/015,222.

English Language Abstract from JPO of JP 63-56529 A.

Notice of Allowance and Fee(s) Due date mailed Jun. 27, 2013 for U.S. Appl. No. 13/162,869.

Office Action notification date Mar. 31, 2015 for U.S. Appl. No. 13/930,711.

Satterfield, C. W., Heterogeneous Catalysis in Industrial Practice, 2nd Edition, McGraw-Hill, Inc., New York, Chapter 1, pp. 1-pp. 30 (1991).

Form PCT/ISA/220, Form PCT/ISA/210), Form PCT/ISA/237) dated Aug. 11, 2014 for PCT/EP2014/063593 which corresponds to U.S. Appl. No. 13/930,711.

"Alkylenes", PAC, 1995, 67, 1307, (Glossary of class names of organice compounds and reactivity intermediates based on structure (IUPAC Recommendations 1995) on p. 1314, obtained from hhttp://goldbook.iupac.org/!00227-plain.html on Mar. 11, 2013.

Form PCT/IB/326, Form PCT/IB/373, and Form PCT/ISA/237 for PCT/IB2012/001219 dated Jan. 9, 2014, which corresponds to U.S. Appl. No. 13/164,869.

Form PCT/ISA/220, Form PCT/ISA/210, and Form PCT/ISA/237 for PCT/IB2012/001219 dated Oct. 19, 2012, which corresponds to U.S. Appl. No. 13/164,869.

Form PCT/ISA/220, Form PCT/ISA/210, and Form PCT/ISA/237 for PCT/EP2013/075815 dated Jul. 9, 2014, which corresponds to U.S. Appl. No. 13/707,993.

Baxendale et al., "The Reduction of Molybdenum(II) Trifluoroacetate by Pulse Radiolysis in Methanol[1]", Journal of the American Chemical Society vol. 98 No. 2, pp. 637-638 (1976).

Burch et al., "Scrambling of Fluoro-, Methoxyl, Dimethylamino-, and Methyl Gropus with Chlorine Atoms of Methoxyl with Dimethylaminol-Groups on Germanium", J. Chm. Soc. (A), pp. 586-589 (1966).

Sartori et al., "Uber die Darstellung und Eigenschaften von Perflouracyloxy-Verbindungen der vierten Gruppe des Periodensystems*", Chem. Ber. vol. 100 No. 6, pp. 2049-2063 (1967).

* cited by examiner

STABLE METAL COMPOUNDS, THEIR COMPOSITIONS AND METHODS

FIELD OF INVENTION

The present invention relates to soluble, multi-ligand-substituted metal compounds with improved stability as well as compositions made from them and methods of their use.

BACKGROUND

Metal oxide films are useful in a variety of applications in the semiconductor industry such as, for example, lithographic hardmasks, underlayers for anti-reflective coatings and electro-optical devices.

As an example, photoresist compositions are used in microlithography processes for making miniaturized electronic components such as in the fabrication of computer chips and integrated circuits. Generally, a thin coating of a photoresist composition is applied to a substrate, such as a silicon based wafer used for making integrated circuits. The coated substrate is then baked to remove a desired amount of solvent from the photoresist. The baked coated surface of the substrate is then image-wise exposed to actinic radiation, such as, visible, ultraviolet, extreme ultraviolet, electron beam, particle beam and X-ray radiation.

The radiation causes a chemical transformation in the exposed areas of the photoresist. The exposed coating is treated with a developer solution to dissolve and remove either the radiation-exposed or the unexposed areas of the photoresist.

The trend towards the miniaturization of semiconductor devices has led to the use of new photoresists that are sensitive to shorter and shorter wavelengths of radiation and has also led to the use of sophisticated multilevel systems to overcome difficulties associated with such miniaturization.

Absorbing antireflective coatings and underlayers in photolithography are used to diminish problems that result from radiation that reflects from substrates which often are highly reflective. Reflected radiation results in thin film interference effects and reflective notching. Thin film interference, or standing waves, result in changes in critical line width dimensions caused by variations in the total light intensity in the photoresist film as the thickness of the photoresist changes. Interference of reflected and incident exposure radiation can cause standing wave effects that distort the uniformity of the radiation through the thickness. Reflective notching becomes severe as the photoresist is patterned over reflective substrates containing topographical features, which scatter light through the photoresist film, leading to line width variations, and in the extreme case, forming regions with complete loss desired dimensions. An antireflective coating film coated beneath a photoresist and above a reflective substrate provides significant improvement in lithographic performance of the photoresist. Typically, the bottom antireflective coating is applied on the substrate and cured followed by application of a layer of photoresist. The photoresist is imagewise exposed and developed. The antireflective coating in the exposed area is then typically dry etched using various etching gases, and the photoresist pattern is thus transferred to the substrate.

Underlayers containing high amount of refractory elements can be used as hard masks as well as antireflective coating. Hard masks are useful when the overlying photoresist is not capable of providing high enough resistance to dry etching that is used to transfer the image into the underlying semiconductor substrate. In such circumstances a material called a hard mask whose etch resistance is high enough to transfer any patterns created over it into the underlying semiconductor substrate. This is made possible because the organic photoresist is different than the underlying hard mask and it is possible to find an etch gas mixture which will allow the transfer of the image in the photoresist into the underlying hard mask. This patterned hard mask can then be used with appropriate etch conditions and gas mixtures to transfer the image from the hard mask into the semiconductor substrate, a task which the photoresist by itself with a single etch process could not have accomplished.

Multiple antireflective layers and underlayers are being used in new lithographic techniques. In cases where the photoresist does not provide sufficient dry etch resistance, underlayers and/or antireflective coatings for the photoresist that act as a hard mask and are highly etch resistant during substrate etching are preferred. One approach has been to incorporate silicon, titanium or other metallic materials into a layer beneath the organic photoresist layer. Additionally, another high carbon content antireflective or mask layer may be placed beneath the metal containing antireflective layer, such as a trilayer of high carbon film/hardmask film/photoresist is used to improve the lithographic performance of the imaging process. Conventional hard masks can be applied by chemical vapor deposition, such as sputtering. However, the relative simplicity of spin coating versus the aforementioned conventional approaches makes the development of a new spin-on hard mask or antireflective coating with high concentration of metallic materials in the film very desirable.

Underlayer compositions for semiconductor applications containing metal oxides have been shown to provide dry etch resistance as well as antireflective properties. Conventional soluble metal compounds to form metal oxide films, such as metal alkoxides, however, have been found to be very unstable to moisture in air creating a variety of issues, including shelf life stability, coating problems and performance shortcomings. Metal oxides have solubility problems in solvents typically used and accepted in the semiconductor industry. Thus there is an outstanding need to prepare spin-on hardmask, antireflective coatings and other underlayers that contain organic solvents soluble, stable metal compounds even after exposure to air, and which can also be strippable in chemical solutions after curing of the film to form metal oxide.

SUMMARY OF THE DISCLOSURE

The present invention relates to novel, soluble, multi-ligand-substituted metal oxide compounds to form metal oxide films with improved stability as well as compositions made from them and methods of their use.

In a first embodiment, disclosed and claimed herein are soluble, multi-ligand-substituted metal compounds of the following structure:

wherein n is about 1 to about 20, $R_1$ is independently a $C_1$-$C_6$ substituted or unsubstituted, branched or unbranched alkyl group or $R_2$, each $R_2$ is the same or different and is at least one of a substituted or unsubstituted aromatic or heteroaromatic group, a $C_6$-$C_{20}$ substituted or unsubstituted, branched or unbranched alkyl or alkenyl group, a —$COR_3$ group, a —$N(R_3)_2$ group, a —$SO_2R_3$ group, a —$SOR_3$ group, or a —$SR_3$ group, wherein each $R_3$ is the same or different and is a substituted or unsubstituted aromatic or heteroaromatic group or a substituted or unsubstituted, branched or unbranched $C_1$-$C_{20}$ alkyl group, alkenyl group, or functionalized group with a structure of -alkylene-$COOR_3'$ or -alkenylene-$COOR_3'$, wherein $R_3'$ is a $C_1$-$C_6$ substituted or unsubstituted, branched or unbranched alkyl group; wherein at least one of the ligands imparts stability to the metal compound. These novel metal compounds are stable even after exposure to air and are also strippable in chemical solutions.

In a further embodiment, disclosed and claimed herein are soluble, multi-ligand-substituted metal compounds of the above embodiment wherein the metal is titanium, zirconium, tantalum, lead, antimony, thallium, indium, ytterbium, gallium, hafnium, aluminum, magnesium, molybdenum, germanium, tin, iron, cobalt, nickel, copper, zinc, gold, silver, cadmium, tungsten, or platinum.

In a further embodiment, disclosed and claimed herein are soluble, multi-ligand-substituted metal compounds of the above embodiments, wherein the metal is the same or is more than one metal when n is about 2 to about 20.

In a further embodiment, disclosed and claimed herein are soluble, multi-ligand-substituted metal compounds of the above embodiments wherein one of $R_2$, is a partially or fully fluorinated alkyl group and/or wherein one of $R_3$ is a partially or fully fluorinated alkyl, alkenyl, aromatic or heteroaromatic group.

In still further embodiments, disclosed and claimed herein are compositions containing the metal compounds of the above embodiments, at least one solvent, and optionally an organic or silicon based crosslinkable polymers when n is about 1-20.

In still further embodiments, disclosed and claimed herein are compositions containing the metal compounds of the above embodiments, at least one solvent, and optionally an organic or silicon based crosslinkable polymers when n is 1.

In still further embodiments, disclosed and claimed herein are compositions of the above embodiments further containing at least one of a thermal acid generator, a thermal base generator, or a thermally activated peroxide.

In still a further embodiment, disclosed and claimed herein are methods of manufacturing an electronic device containing the steps of applying a composition of any of the above embodiments onto a substrate, baking at about 120° C. to about 350° C. from about 30 to about 120 seconds and optionally removing the composition using a stripper.

DETAILED DESCRIPTION

As used herein, the conjunction "and" is intended to be inclusive and the conjunction "or" is not intended to be exclusive unless otherwise indicated. For example, the phrase "or, alternatively" is intended to be exclusive.

As used herein, the term "and/or" refers to any combination of the foregoing elements including using a single element.

As used herein the term "alkyl" refers to straight, or cyclic chain alkyl substituents as well as any of their branched isomers.

As used herein the term "alkenyl" refers to straight or cyclic chain alkenyl substituents containing unsaturated carbon-carbon bond as well as any of their branched isomers.

As used herein the term "alkylene" refers to straight or cyclic chain alkylene substituents as well as any of their branched isomers.

As used herein the term "alkenylene" refers to straight or cyclic chain alkenylene substituents containing unsaturated carbon-carbon bond as well as any of their branched isomers.

As used herein the term "silicon-based polymer" refers to silicon polymers as well as organosilicon polymers and include the lower mer materials such as dimer, trimer and the like.

As used herein the terms "composition" and "formulation" are used interchangeable and mean the same thing.

Disclosed and claimed herein are soluble, multi-ligand-substituted metal compounds of the following structure:

The metal, M, can be chosen from a list of suitable metals, including, for example, titanium, zirconium, tantalum, lead, antimony, thallium, indium, ytterbium, gallium, hafnium, aluminum, magnesium, molybdenum, germanium, tin, iron, cobalt, nickel, copper, zinc, gold, silver, cadmium, tungsten, or platinum as well as other transition metals. The metal compound may be monoatomic, n being about 1. The metal compound may also be polyatomic, n being about 2 to about 20 creating a chain of alternating metal-oxygen segments. The polyatomic compound may contain only one type of metal atom, such as, for example, titanium, or they may have other metals dispersed into the metal-oxo backbone, such as silicon and zirconium. The amount of each metal in a mixed metal polyatomic metal compound can range from 0.001% to 99.999% depending on the desired characteristics of the final cured metal oxide layer. These novel metal compounds are stable even after exposure to air and are also strippable in chemical solutions.

$R_1$ may be a $C_1$-$C_6$ alkyl group, as well as any of their branched and/or cyclic isomers and may be unsubstituted or substituted with, for example, halogens (such as fluorine, chlorine, bromine, etc) or $R_1$ may be $R_2$. Additionally two $R_1$ groups may be part of the same ligand such as, for example, the acetylacetone, the acetylacetates, and other diketones.

Each $R_2$ may be the same or different. They can be substituted or unsubstituted aromatic groups, such as for example, phenyl, naphthyl, anthracenyl groups and the like. $R_2$ may also be heteroaromatic groups, such the nitrogen heterocycles, such as, for example, pyridine, pyrrole, pyrazine or the sulfur heterocycles, such as, for example, thiophene. $R_2$ may be a $C_6$-$C_{20}$ substituted or unsubstituted alkyl or alkenyl group, or their branched and/or cyclic isomers. These may also be substituted, for example, with halogens such as fluorine. $R_2$ may also be a —$COR_3$ group, a —$N(R_3)_2$ group, a —$SO_2R_3$ group, a —$SOR_3$ group, or a —$SR_3$ group, wherein $R_3$ is the same or different and are a substituted or unsubstituted aromatic or heteroaromatic group or a substituted or unsubstituted, branched, unbranched and/or cyclic $C_1$-$C_{20}$ alkyl group, alkenyl group, or functionalized alkylene with a structure of -alkylene-$COOR_{40}$' or -alkenylene-$COOR_3$', wherein $R_3$' is a $C_1$-$C_6$ substituted or unsubstituted, branched or unbranched alkyl, or cyclic group.

The molar equivalent of $R_2$ is >10% of the total moles of the coordinated ligands in above structure depending on the size, the volatility and the hydrophobicity of the $R_2$ ligand. Usually the amount of the $R_2$ can be up to 100 mole %, or 40-80 mole % of the total ligands ($R_1$+$R_2$). Other ligands such as chelating agents can also be used to stabilize the metal compound. Examples of chelating ligands are acetylacetone, benzoylacetone, 4,4,4-Trifluoro-1-phenyl-1,3-butanedionate, and ethyl acetoacetate.

Thus each $R_2$ may be the same or different and may be an unsaturated ester such as —CO—CH=CH—$COOR_3$' or —CO—CH=C($CH_3$)—$COOR_3$', or an aromatic ester such as —CO—$C_6H_4$—$COOR_3$', an alkyl ester such as —CO—$CH_2CH_2$—$COOR_3$' or —CO—$CH_2CH_2CH_2$—$COOR_3$', or a cycloaliphatic ester such as —CO—$C_6$—$H_{10}$—$COOR_3$' wherein $C_6H_{10}$ is a cyclohexyl group.

It was surprisingly found that the multi-ligand-substituted metal oxides as described above were very stable to moisture and air compared to conventional metal oxides, such as, Ti(O-butyl)$_4$, as shown in Table 3, below. Additionally, by adding various classes of ligands to the metal oxides, they were solubilized into a variety of solvents useful for spin-on coating and for solubilizing other ingredients when composite compositions were used. Coating quality was also improved when these metal compounds replaced the conventional metal oxides used in underlayer coatings.

The preparation of the multi-ligand-substituted metal compound of the current disclosure is prepared from their alkoxides or acetylacetonates (acac), as described below. The alkoxy or acac metal compounds are reacted with anhydrides, cyclic anhydrides, carboxylic acids, sulfonic acid, amides, hydroxylamines, sulfonates, sulfinates, sulfenates, acrylic acids and/or methacrylic acids to replace a portion of the alkoxy or acac groups. Other higher molecular weight alkoxy metal compounds, or those with specific functional groups on the ligand, can be obtained from higher molecular weight or functionalized alcohols. The target amount of ligand substitution in the reaction is greater than 10 mole % of the total coordination sites depending on the size, the volatility, solubility and the hydrophobicity of the ligand doing the substituting.

It should be noted that more than one ligand may be used to react with the alkoxy metal as desired.

Figure 1A:
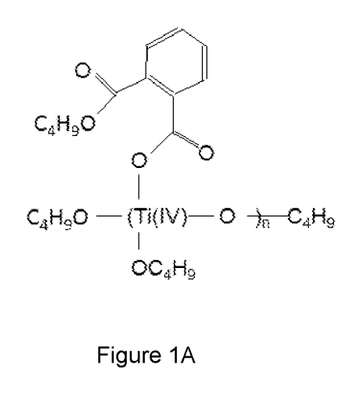
FIG. 1A-1I are examples of soluble, multi-ligand-substituted metal compounds of the current disclosure.
Figure 1B:
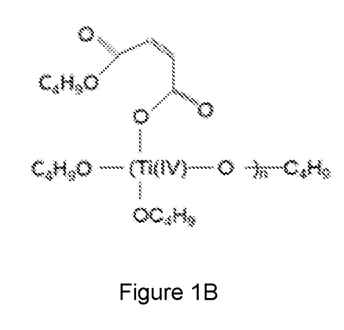
Figure 1C:
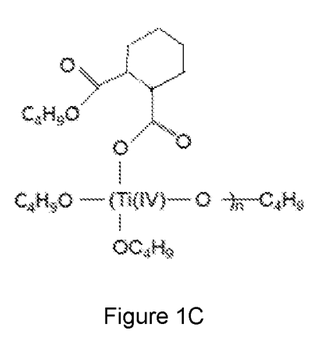
Figure 1D:
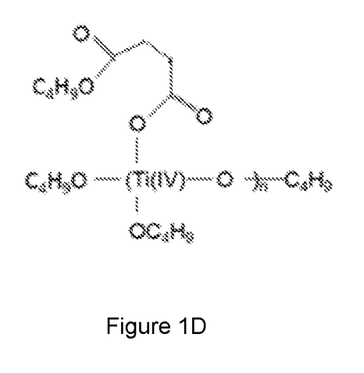
Figure 1E:
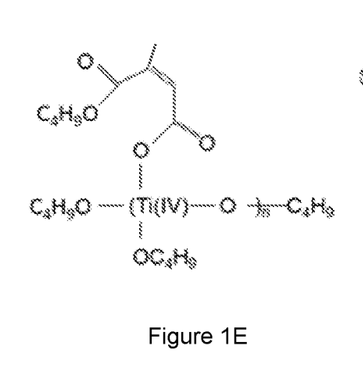
Figure 1F:
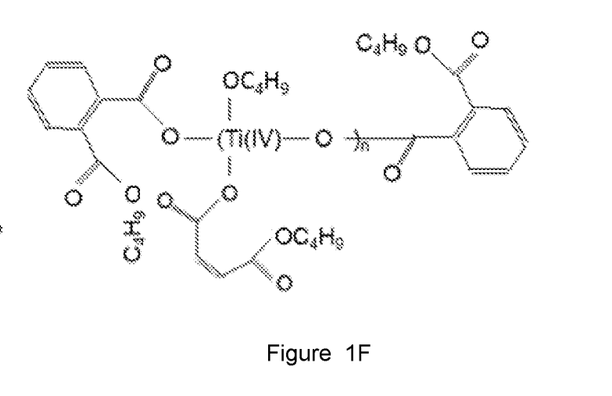
Figure 1G:
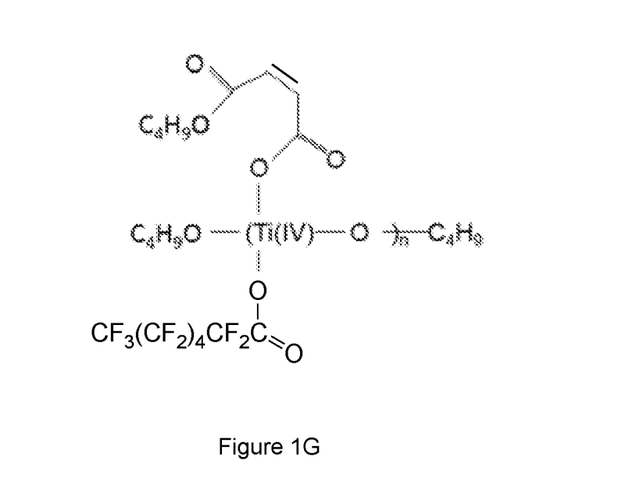
Figure 1H:
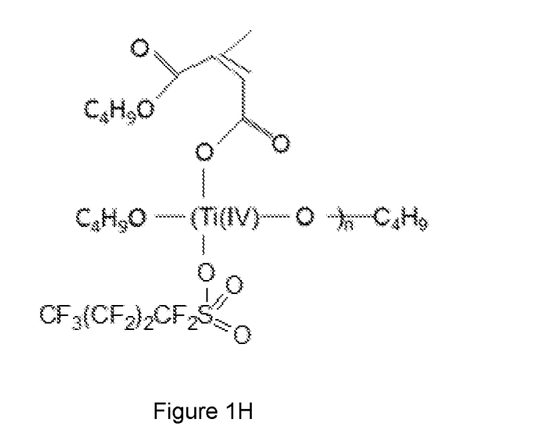
Figure 1I:
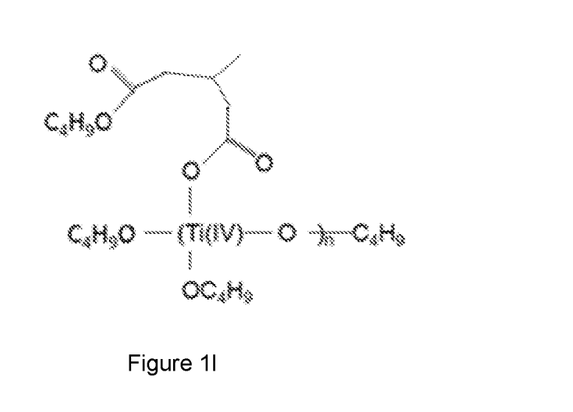
Figure 2:
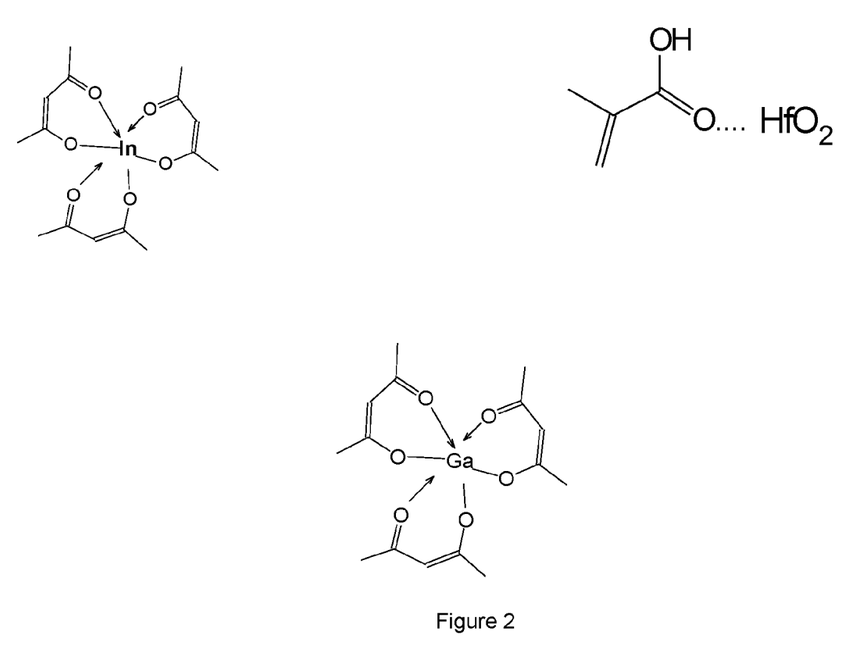
FIG. 2 shows examples of soluble, multi-ligand-substituted metal complexes.

Examples of soluble, multi-ligand-substituted metal compound of the current disclosure are shown in FIGS. 1-2.

The multi-ligand-substituted metal compounds of the current disclosures are used to prepare metal oxide containing layers useful in the semiconductor industry as well as associated industries. When the n is about 2 to about 20, for example, about 4 to about 20, in the compound formula above, the compound can be dissolved in a suitable solvent and used without any other additives. When n is 1, an additional film forming organic or silicon based polymer is used, such as, for example, poly(meth)acrylics, poly(meth)acrylates, and condensation polymers such as polyesters, novolac resins, siloxane resins or organosilsesquioxanes. These polymers may be used alone or in combination with each other depending on the desired properties of the final film after curing. These polymers are generally crosslinking polymers, containing any of a number of the same or different crosslinking substituents, such as, for example, epoxy, hydroxy, thiols, amines, amides, imides, esters, ethers, ureas, carboxylic acids, anhydrides, and the like. Other examples of crosslinking groups include the glycidyl ether group, glycidyl ester group, glycidyl amino group, methoxymethyl group, ethoxy methyl group, benzyloxymethyl group, dimethylamino methyl group, diethylamino methyl group, dimethylol amino methyl group, diethylol amino methyl group, morpholino methyl group, acetoxymethyl group, benzyloxy methyl group, formyl group, acetyl group, vinyl group and isopropenyl group.

Figure 3:
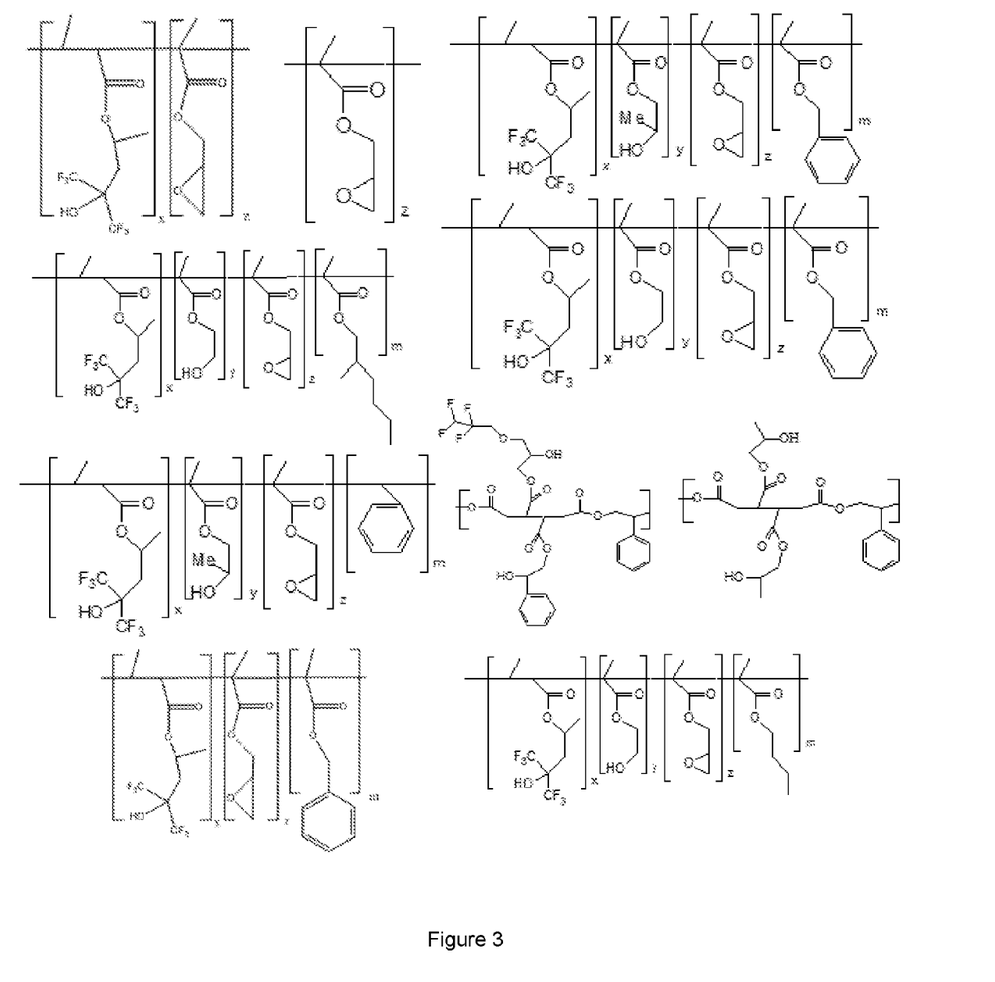
FIG. 3 shows examples of the organic polymer as used in the formulations.

An organic or silicon based crosslinkable polymer is admixed with the metal components when n=1. Optionally an organic or silicon based crosslinkable polymers may be admixed with the metal components when n is about 2 to about 20. The organic polymer contains crosslinkable groups such as, for example, hydroxyl, epoxy, amide, urea or carboxylic acid. Examples of the crosslinkable polymers are described in FIG. 3. Silicon based polymers are such as crosslinkable polysiloxanes. Organic polymers may be polyvinyls, polyacrylics, polyesters, etc.

The organic polymer of the novel composition, may comprise a unit with a fluoroalcohol group of structure (1), and a unit with an epoxy group of structure (2), where, $R_4$ to $R_9$ are independently selected from hydrogen and $C_1$-$C_4$ alkyl, W is a divalent linking group (such as arylene, a carbonyloxy (—C(=O)—O—) and a carbonyloxyalkylene (—C(=O)—O—$W_3$—) where $W_3$ is selected from a $C_1$ to $C_{20}$ alkylene moiety, a fully fluorinated ($C_1$-$C_{20}$) alkylene group and a partially fluorinated ($C_1$-$C_{20}$) alkylene group), $Rf_1$ and $Rf_2$ is independently selected from fully or partially fluorinated ($C_1$-$C_6$) alkyl group; $W_1$ is selected from an arylene linking group, a carbonyl (—(C=O)) linking group, and a carbonyloxyalkylene linking group (—C(=O)—O—$W_4$—) where $W_4$ is selected from a group consisting of $C_1$ to $C_6$ alkylene moiety, fluorinated ($C_1$-$C_6$) alkylene group and partially fluorinated ($C_1$-$C_6$) alkylene group; and $W_2$ a ($C_1$-$C_6$) alkylene moiety. The polymer may contain only monomeric units with structure 1 and structure 2, or may optionally contain other monomeric units. Specific examples of $W_3$ and $W_4$ are independently methylene, ethylene, propylene, isopropylene, and 1-hexylethylene, pentafluoropropylene, 2,2,2-trifluoroethylene and heptafluorobutylene. Specific examples of $Rf_1$ and $Rf_2$ are trifluoromethyl, pentafluoropropyl and 2,2,2-trifluoroethyl, heptafluorobutyl. Specific examples of $W_2$ are methylene, ethylene, propylene, isopropylene, etc.

The organic polymer may contain units of structure (1) and (2), and may additionally contain the optional recurring unit (3) where $R_{10}$ to $R_{12}$ are independently selected from hydrogen and $C_1$-$C_4$ alkyl (3)

where $W_5$ is selected from a direct valance bond, an arylene group, an ester (C(=O)—O—$R_{13}$) group, a $C_1$-$C_{20}$ alkylene group and mixtures thereof, where $R_{13}$ is selected from $C_1$-$C_{20}$ alkylene, $C_1$-$C_{20}$ alkylenearylene, arylene and substituted arylene. Specific examples of the monomer used to obtain unit (3) are 2-hydroxyethylmethacrylate, 2-hydroxypropylmethacrylate, 2-hydroxybutylmethacrylate and hydroxystyrene.

The underlayer organic polymer may contain at least a unit of structure 1 and one of structure 2 or one of structure 3, and may additionally contain the optional recurring unit (4), where, $R_{14}$ to $R_{16}$ are independently selected from hydrogen, nitrile (CN) and $C_1$-$C_4$ alkyl, $R_{17}$ is an aryl group or an ester (—C(=O)—O—$R_{18}$) group, where $R_{18}$ is selected from a group consisting of a $C_1$-$C_{20}$ alkyl, $C_1$-$C_{20}$ alkylenearyl, aryl, substituted aryl, fluorinated alkyl group, partially fluorinated alkyl group or mixtures thereof. Other monomeric units may also be present in the organic polymer. Specific examples of the monomer used to obtain unit (4) are styrene, benzylmethacrylate, butylmethacrylate, 2-ethylhexyl methacrylate, benzylacrylate and butylacrylate.

(4)

In the novel underlayer composition the polymer comprises the fluoroalcohol group ranging between 10 and 90 mole % and the epoxy group ranging between 10 and 90 mole %.

In the embodiment of the polymer where only units of structure 1 and one of structure 2 and structure 3 are present, unit (1) can range from about 10-80 mole % or 20-60 mole %; while repeat unit (2) or (3) can range from about 20-90 mole % or about 30-70 mole %. In the embodiment of the polymer where at least three types of repeat units having structure 1, 2 and 3 or 4 are present, unit 1 can range from about 10-70 mole % or about 20-50 mole %, recurring unit 2 can range from about 10-70 mole % or about 20-50%, and recurring unit 3 or 4 can range from about 1-50 mole % or about 5-40 mole %. In the embodiment of the polymer where at least 4 types of repeat units having structures 1, 2, 3 and 4 are present, unit 1 ranges from 10-70 mole % or 20-50%, repeat unit 2 can range from 10-70 mole % or about 20-50 mole %, repeat unit 3 can range from about 1-40 mole % or about 5-30 mole %, and repeat unit 4 can range from about 1-30 mole % or about 5-25 mole %.

Suitable solvents for the underlayer coating composition may include, for example, lower alcohols ($C_1$-$C_6$) such as isopropanol, n-butanol, t-butanol, 1-pentanol and 4-methyl-2-pentanol, a glycol such as ethylene glycol and propylene glycol, a glycol ether derivative such as ethyl cellosolve, methyl cellosolve, propylene glycol monomethyl ether, diethylene glycol monomethyl ether, diethylene glycol monoethyl ether, dipropylene glycol dimethyl ether, propylene glycol n-propyl ether, or diethylene glycol dimethyl ether; a glycol ether ester derivative such as ethyl cellosolve acetate, methyl cellosolve acetate, or propylene glycol monomethyl ether acetate; carboxylates such as ethyl acetate, n-butyl acetate and amyl acetate; carboxylates of di-basic acids such as diethyloxylate and diethylmalonate; dicarboxylates of glycols such as ethylene glycol diacetate and propylene glycol diacetate; and hydroxy carboxylates such as methyl lactate, ethyl lactate, ethyl glycolate, and ethyl-3-hydroxy propionate; a ketone ester such as methyl pyruvate or ethyl pyruvate; an alkoxy alcohol such as 2-methoxyethanol, ethoxyethanol, an alkoxycarboxylic acid ester such as methyl 3-methoxypropionate, ethyl 3-ethoxypropionate, ethyl 2-hydroxy-2-methylpropionate, or methylethoxypropionate; a ketone derivative such as methyl ethyl ketone, acetyl acetone, cyclopentanone, cyclohexanone or 2-heptanone; a ketone ether derivative such as diacetone alcohol methyl ether; a ketone alcohol derivative such as acetol or diacetone alcohol; lactones such as butyrolactone and gamma-velaro lactone; an amide derivative such as dimethylacetamide or dimethylformamide, anisole, and mixtures thereof.

The novel composition comprising metal compound, may include other components which enhance the performance of the coating, e.g. lower alcohols ($C_1$-$C_6$ alcohols), alkoxyalcohols, lactones, $C_1$-$C_{20}$ alkyl carboxylic acids, surface leveling agents (<5 weight % of total solids), dialkoxy bis(betadiketoesters) (1-20 weight % or 5-10 weight % of total solids), dialkoxy bis(beta diketone) (1-20 weight % or 5-10 weight % of total solids), thermal acid generator, photoacid generator, etc. Dialkoxy bis(betadiketoesters) and dialkoxy bis(beta diketone) can be acetylacetone, benzoylacetone, 4,4,4-Trifluoro-1-phenyl-1,3-butanedione, and ethyl acetoacetate. Surface leveling agents or surfactants can be polyethylene glycol dodecyl ether, polyoxyethylene oleyl ether, polyethylene glycol octadecyl ether, polyethylene glycol tert-octylphenyl ether, fluorine based surfactant, and silicon based surfactant. Surfactants with the following trade names may be used, Brij30, Brij52, Triton X-100, FC430, etc.

To further crosslink the composition, crosslinking additives may be added, including, for example, bisphenol A-based epoxy compounds, bisphenol F-based epox compounds, bisphenol S-based epoxy compounds, the novolac resin-based epoxy, poly(hydroxystyrene)-based epoxy compounds, melamine compounds, benzoguanamine compounds, and urea compounds.

Thermally activated catalysts, such as thermal acid generators, may also be added to the composition to aid in crosslinking during thermal curing of the coated composition. The thermal acid generator can be activated at above 90° C. for example above 120° C., and above 150° C. Examples of thermal acid generators include metal-free sulfonium salts and iodonium salts, such as triarylsulfonium, dialkylarylsulfonium, and diarylakylsulfonium salts of strong non-nucleophilic acids, alkylaryliodonium, diaryliodonium salts of strong non-nucleophilic acids; and ammonium, alkylammonium, dialkylammonium, trialkylammonium, tetraalkylammonium salts of strong non nucleophilic acids. 2-nitrobenzyl esters of alkyl or arylsulfonic acids and other esters of sulfonic acid which thermally decompose to give free sulfonic acids. Other examples include diaryliodonium perfluoroalkylsulfonates, diaryliodonium tris(fluoroalkylsulfonyl)methide, diaryliodonium bis(fluoroalkylsulfonyl)methide, diaryliodonium bis(fluoroalkylsulfonyl)imide, diaryliodonium or quaternary ammonium perfluoroalkylsulfonate. Examples of labile esters: 2-nitrobenzyl tosylate, 2,4-dinitrobenzyl tosylate, 2,6-dinitrobenzyl tosylate, 4-nitrobenzyl tosylate; benzenesulfonates such as 2-trifluoromethyl-6-nitrobenzyl 4-chlorobenzenesulfonate, 2-trifluoromethyl-6-nitrobenzyl 4-nitro benzenesulfonate; phenolic sulfonate esters such as phenyl, 4-methoxybenzenesulfonate; quaternary ammonium tris(fluoroalkylsulfonyl)methide, and quaternaryalkyl ammonium bis(fluoroalkylsulfonyl)imide, alkyl ammonium salts of organic acids, such as triethylammonium salt of 10-camphorsulfonic acid. A variety of aromatic (anthracene, naphthalene or benzene derivatives) sulfonic acid amine salts can be employed as the TAG, including those disclosed in U.S. Pat. Nos. 3,474,054, 4,200,729, 4,251,665 and 5,187, 019. The TAG may have a very low volatility at temperatures between 170-220° C.

Thermally activated peroxides may also be used in the current composition, such as, for example, benzoyl peroxide, 3,5-dichlorobenzoperoxide and the like.

The compositions of the current disclosure contain greater than 20 weight % of the multi-ligand-substituted metal compound based on solids, such as, for example, greater than weight 50% or greater than 90 weight % based on solids. Two or more metal compounds with the same or different metal can be used in formulations. The polymer, when used, is less than about 80 weight % based on solids, such as, for example, less than 50 weight %, less than 10 weight % based on solids. The crosslinking additive is present between 2-30 weight % based on solids. Other additives typical of coating additive may be added, such as, for example, wetting agents, surfactants, anti-foam agent, thixotropic agents and the like.

The total percent solids in the chosen solvent or solvent blend is between about 1-about 40% wt/wt, such as, for example, about 2-about 30% wt/wt.

The novel compound and compositions made comprising the novel compound are stable when exposed to air and then stored. The materials may be exposed to air for up to 24 hours and then stored for at least 1 week without any deterioration of lithographic properties, such as coating defects. Furthermore, the novel materials can be removed by wet strippers, such as chemical solutions that remove the cured film.

The compositions of the current disclosure can be coated onto the surface of a substrate such as low dielectric constant materials, silicon, silicon substrates coated with a metal surface, copper coated silicon wafer, copper, aluminum, polymeric resins, silicon dioxide, metals, doped silicon dioxide, silicon nitride, tantalum, polysilicon, ceramics, aluminum/copper mixtures, any of the metal nitrides such as AlN; gallium arsenide and other such Group III/V compounds. The substrate may also be other antireflective coatings or underlayers, such as high carbon underlayers coated over the above mentioned substrates. The substrate may comprise any number of layers made from the materials described above.

The composition of the current disclosure is coated on the substrate using techniques well known to those skilled in the art, such as dipping, spin coating or spraying. The film thickness of the underlayer coating ranges from about 3 nm to about 500 nm, such as, for example, about 5 nm to about 250 nm. The coating may further heated on a hot plate or convection oven for a sufficient length of time to remove a majority of the solvent and induce curing. The cure temperature may be from about 90° C. to about 350° C. for about 30 seconds to about 10 minutes, such as, for example, from about 120° C. to about 250° C. for about 1 to about 2 minutes. The composition may be coated over other layers of antireflective coatings, such as a high carbon (greater than 80% or 85% or 90%) content antireflective coating.

The crosslinkability and the optical parameters of the materials can be adjusted to provide desired characteristics. The compositions and process conditions can be optimized such that the films pass soaking tests in both casting solvent and photoresist developers without additional crosslinking agent and catalysts. The composition of the cured film contains between about 5 to about 90% of metal oxide wt/wt or between about 10 to about 70% of metal oxide wt/wt at normal baking conditions.

The cured metal oxide film can be advantageously removed using a chemical stripping agent, such as acid, base, peroxide, and mixture thereof. For example, 85% phosphoric acid, diluted sulfuric acid, 3% HF, 10% TMAH, 10% hydrogen peroxide, aqueous alkaline peroxides and mixtures thereof. Stripping time ranges from about 5 seconds to about 120 seconds at about room temperature to about 70° C. depending on the film curing conditions. Other stripping processes may be employed in conjunction with processing conditions of the metal oxide film. For example, when the film is cured at a lower temperature or a shorter time, the stripper may be diluted, the time may be shortened and/or the temperature of stripping may be reduced. Results are shown in Table 4.

The soluble, multi-ligand-substituted metal compounds of the current disclosure, their compositions and methods of use can be used to prepare antireflective layer. Sufficient chromophore groups are present, and the refractive indices of the underlayer n (refractive index) can range from about 1.5 to about 2.2 and k (extinction coefficient) (part of the complex refractive index $n_c = n-jk$) can range from about 0.1 to about 0.8 at 193 nm exposure wavelength. The novel coatings are useful as a hard mask. The n and k values can be calculated using an ellipsometer, such as the J. A. Woollam WVASE VU-32™ Ellipsometer. The exact values of the optimum ranges for k and n are dependent on the exposure wavelength used and the type of application. Typically for 193 nm the preferred range for k is about 0.1 to about 0.8, and for 248 nm the preferred range for k is about 0.15 to about 0.8, however, other exposure wavelengths such as, for example DUV and beyond DUV can be used and the compositions tuned to work in conjunction with them.

The photoresist compositions are applied over the novel coating by such processes as spin coating, and the like. After coating, the solvent is removed to a level wherein the coating can be properly exposed. In some cases a residual of 5% solvent may remain in the coating while in other cases less than 1% is required. Drying can be accomplished by hot plate heating, convection heating, infrared heating and the like. The coating is imagewise exposed with actinic radiation through a mark containing a desired pattern. A film of photoresist is coated on top of the underlayer coating and baked to substantially remove the photoresist solvent. An edge bead remover may be applied after the coating steps to clean the edges of the substrate using processes well known in the art.

Photoresists can be any of the types used in the semiconductor industry, provided the photoactive compound in the photoresist and the antireflective coating substantially absorb at the exposure wavelength used for the imaging process. Photoresists useful for immersion lithography are preferred. Typically, photoresists suitable for imaging with immersion lithography may be used, where such photoresists have a refractive index higher than 1.85 and also are hydrophobic having water contact angle in the range of 75° to 95°.

To date, there are several major deep ultraviolet (uv) exposure technologies that have provided significant advancement in miniaturization, and have actinic radiation of 250 nm to 10 nm, such as 248 nm, 193 nm, 157 and 13.5 nm. Chemically amplified photoresist are often used. Photoresists for 248 nm have typically been based on substituted polyhydroxystyrene and its copolymers/onium salts, such as those described in U.S. Pat. No. 4,491,628 and U.S. Pat. No. 5,350,660. On the other hand, photoresists for exposure at 193 nm and 157 nm require non-aromatic polymers since aromatics are opaque at this wavelength. U.S. Pat. No. 5,843,624 and U.S. Pat. No. 6,866,984 disclose photoresists useful for 193 nm exposure. Generally, polymers containing alicyclic hydrocarbons are used for photoresists for exposure below 200 nm. Alicyclic hydrocarbons are incorporated into the polymer for many reasons, primarily since they have relatively high carbon to hydrogen ratios which improve etch resistance, they also provide transparency at low wavelengths and they have relatively high glass transition temperatures. U.S. Pat. No. 5,843,624 discloses polymers for photoresist that are obtained by free radical polymerization of maleic anhydride and unsaturated cyclic monomers. Any of the known types of 193 nm photoresists may be used, such as those described in U.S. Pat. No. 6,447,980 and U.S. Pat. No. 6,723,488, and incorporated herein by reference. Two basic classes of photoresists sensitive at 157 nm, and based on fluorinated polymers with pendant fluoroalcohol groups, are known to be substantially transparent at that wavelength. One class of 157 nm fluoroalcohol photoresists is derived from polymers containing groups such as fluorinated-norbornenes, and are homopolymerized or copolymerized with other transparent monomers such as tetrafluoroethylene (U.S. Pat. No. 6,790,587, and U.S. Pat. No. 6,849,377) using either metal catalyzed or radical polymerization. Generally, these materials give higher absorbencies but have good plasma etch resistance due to their high alicyclic content. More recently, a class of 157 nm fluoroalcohol polymers was described in which the polymer backbone is derived from the cyclopolymerization of an asymmetrical diene such as 1,1,2,3,3-pentafluoro-4-trifluoromethyl-4-hydroxy-1,6-heptadiene (U.S. Pat. No. 6,818,258) or copolymerization of a fluorodiene with an olefin (U.S. Pat. No. 6,916,590). These materials give acceptable absorbance at 157 nm, but due to their lower alicyclic content as compared to the fluoro-norbornene polymer, have lower plasma etch resistance. These two classes of polymers can often be blended to provide a balance between the high etch resistance of the first polymer type and the high transparency at 157 nm of the second polymer type. Photoresists that absorb extreme ultraviolet radiation (EUV) of 13.5 nm are also useful and are known in the art. Thus photoresists absorbing in the range of about 12 nm to about 250 nm are useful. The novel coatings can also be used in process with nanoimprinting and e-beam resists.

After the coating process, the photoresist is imagewise exposed. The exposure may be done using typical exposure equipment. The exposed photoresist is then developed in an aqueous developer to remove the treated photoresist. The developer is preferably an aqueous alkaline solution comprising, for example, tetramethylammonium hydroxide (TMAH), typically 2.38 weight % TMAH. The developer may further comprise surfactant(s). An optional heating step can be incorporated into the process prior to development and after exposure.

The process of coating and imaging photoresists is well known to those skilled in the art and is optimized for the specific type of photoresist used. The photoresist patterned substrate can then be dry etched with an etching gas or mixture of gases, in a suitable etch chamber to remove the exposed portions of the underlayers and optional other antireflective coatings. Various etching gases are known in the art for etching underlayer coatings, such as those comprising $O_2$, $CF_4$, $CHF_3$, $Cl_2$, HBr, $SO_2$, CO, etc. In one embodiment, the article comprises a semiconductor substrate with a high carbon antireflective film, over which the novel metal layer is coated. A photoresist layer is coated above this. The photoresist is imaged as disclosed above and the metal underlayer is dry etched using gases comprising fluorocarbons. After the metal underlayer is etched, the high carbon film can be dry etched using oxygen or oxygen mixtures. Advantageously the novel metal layer may be removed using a stripper which is a chemical solution, as described herein.

Each of the documents referred to above are incorporated herein by reference in its entirety, for all purposes. The following specific examples will provide detailed illustrations of the methods of producing and utilizing compositions of the present invention. These examples are not intended, however, to limit or restrict the scope of the invention in any way and should not be construed as providing conditions, parameters or values which must be utilized exclusively in order to practice the present invention.

EXAMPLES

The refractive index (n) and the extinction coefficient (k) values of the antireflective coating in the Examples below were measured on a J. A. Woollam VASE32 ellipsometer.

The molecular weight of the polymers was measured on a Gel Permeation Chromatograph.

Synthesis Example 1

40 g of Ti(IV) tetrabutoxide polymer (Ti(IV)BTP), 10 g of phthalic anhydride and 50 g of benzene were mixed by stirring and heated in a flask under nitrogen. The reaction was maintained at 60° C. for about one hour. After cooling down to room temperature, a majority of the solvent was removed by distillation and drying under vacuum. Proton NMR showed no anhydride present in the product.

Synthesis Example 2

40 g of Ti(IV)BTP polymer, 10.4 g of 1,2-cyclohexanedicarboxylic anhydride and 50.4 g of cyclohexane were mixed by stirring and heated in a flask under nitrogen. The reaction was maintained at 60° C. for about one hour. After cooling down to room temperature, a majority of the solvent was removed by distillation and drying under vacuum. Proton NMR showed no anhydride present in the product.

Synthesis Example 3

40 g of Ti(IV)BTP polymer, 10 g of phthalic anhydride and 50 g of propylene glycol monomethyl ether acetate (PG- MEA)/propylene glycol monomethyl ether (PGME) 70:30 were mixed by stirring and heated in a flask under nitrogen. The reaction was maintained at 50° C. for about two hours. After cooling down to room temperature, the product with 50% solid content was stored in a brown bottle. Proton NMR showed no anhydride present in the product and was similar to that of Synthesis Example 1 except for the signals due to PGMEA/PGME solvents.

Synthesis Example 4

40 g of Ti(IV)BTP polymer, 10.4 g of 1,2-cyclohexanedicarboxylic anhydride and 50.4 g of PGMEA/PGME 70:30 were mixed by stirring and heated in a flask under nitrogen. The reaction was maintained at 50° C. for about two hours. After cooling down to room temperature, the product with 50% solid content was stored in a brown bottle. Proton NMR showed no anhydride present in the product and was similar to that of Synthesis Example 2 except for the signals due to PGMEA/PGME solvents.

Synthesis Example 5

40 g of Ti(IV)BTP polymer, 19.8 g of maleic anhydride and 59.8 g of cyclohexane were mixed by stirring and heated in a flask under nitrogen. The reaction was maintained at 60° C. for about 2 hours. After cooling down to room temperature, the product with 50% solid content was stored in a brown bottle. Proton NMR showed no anhydride present in the product. FT-IR in cyclohexane showed a reduction of the peak at ~1100 cm$^{-1}$ due to Ti-OBu resonance and a new broad peak at 1570 cm$^{-1}$ due to Ti—OC(=O)R resonance.

Synthesis Example 6

40 g of Ti(IV)BTP polymer, 19.8 g of maleic anhydride and 59.8 g of PGMEA/PGME 70:30 were mixed by stirring and heated in a flask under nitrogen. The reaction was maintained at 50° C. for about 3 hours. After cooling down to room temperature, the product with 50% solid content was stored in a brown bottle. Proton NMR showed no anhydride present in the product. A sample was dissolved in cyclohexane and FT-IR was taken in cyclohexane. The spectrum showed a reduction of the peak at ~1100 cm$^{-1}$ due to Ti-OBu resonance and a new broad peak at ~1600 cm$^{-1}$ due to Ti—OC(=O)R resonance.

Synthesis Example 7

40 g of Ti(IV)BTP polymer, 30 g of citraconic anhydride and 70 g of PGMEA/PGME 70:30 were mixed by stirring and heated in a flask under nitrogen. The reaction was maintained at 50° C. for about 4 hours. After cooling down to room temperature, the product with 50% solid content was stored in a brown bottle.

Synthesis Example 8

40 g of Ti(IV)BTP polymer, 22.5 g of citraconic anhydride and 62.5 g of PGMEA/PGME 70:30 were mixed by stirring and heated in a flask under nitrogen. The reaction was maintained at 50° C. for about 3 hours. After cooling down to room temperature, the product with 50% solid content was stored in a brown bottle.

Synthesis Example 9

40 g of Ti(IV)BTP polymer, 10.3 g of cis-1,2,3,6-tetrahydrophthalic anhydride and 50.3 g of PGMEA/PGME 70:30 were mixed by stirring and heated in a flask under nitrogen. The reaction was maintained at 50° C. for about two hours. After cooling down to room temperature, the product with 50% solid content was stored in a brown bottle. Proton NMR showed no anhydride present in the product.

Synthesis Example 10

40 g of Ti(IV)BTP polymer, 10 g of phthalic anhydride and 50 g of PGMEA/PGME 70:30 were mixed by stirring and heated in a flask under nitrogen. The reaction was maintained at 50° C. for about 2 hours. 15 g of citraconic anhydride in 15 g of PGMEA/PGME 70:30 was slowly added to the reaction vessel. The reaction was allowed to continue for another 3 hours at 50° C. After cooling down to room temperature, the product with 50% solid content was stored in a brown bottle. Proton NMR showed no anhydride present in the product.

Synthesis Example 11

40 g of Ti(IV)BTP polymer, 10 g of phthalic anhydride and 50 g of PGMEA/PGME 70:30 were mixed by stirring and heated in a flask under nitrogen. The reaction was maintained at 50° C. for about 2 hours. 13.2 g of maleic anhydride in 13.2 g of PGMEA/PGME 70:30 was slowly added to the reaction vessel. The reaction was allowed to continue for another 3 hours at 50° C. After cooling down to room temperature, the product with 50% solid content was stored in a brown bottle. Proton NMR showed no anhydride present in the product.

Synthesis Example 12

40 g of Ti(IV)BTP polymer, 19.8 g of maleic anhydride and 59.8 g of PGMEA/PGME 70:30 were mixed by stirring and heated in a flask under nitrogen. The reaction was maintained at 50° C. for about 2 hours. 6.1 g of perfluoroheptanoic acid in 6.1 g of PGMEA/PGME 70:30 was slowly added in the reaction vessel. The reaction was allowed to continue for another 2 hours at 50° C. After cooling down to room temperature, the product with 50% solid content was stored in a brown bottle. Proton NMR showed no anhydride present in the product.

Synthesis Example 13

40 g of Ti(IV)BTP polymer, 13.2 g of maleic anhydride and 53.2 g of cyclohexane were mixed by stirring and heated in a flask under nitrogen. The reaction was maintained at 60° C. for about 1 hour. 11.1 g of pentafluoropropanoic acid in 11.1 g of cyclohexane was slowly added in the reaction vessel. The reaction was allowed to continue for another 1 hour at 60° C. After cooling down to room temperature, the product with 50% solid content was stored in a brown bottle. FT-IR in cyclohexane showed a reduction of the peak at ~1100 cm$^{-1}$ due to Ti-OBu resonance, a new broad peak at 1570 cm$^{-1}$ due to Ti—OC(=O)R resonance and a new broad peak at 1650 cm$^{-1}$ due to Ti—OC(=O)Rf resonance.

Synthesis Example 14

40 g of Ti(IV)BTP polymer, 22.5 g of citraconic anhydride and 50 g of PGMEA/PGME 70:30 were mixed by stirring and heated in a flask under nitrogen. The reaction was maintained at 50° C. for about 2 hours. 2.5 g of nonafluorobutane-1-sulfonic acid in 15 g of PGMEA/PGME 70:30 was slowly added in the reaction vessel. The reaction was allowed to continue for another 2 hours at 50° C. After cooling down to room temperature, the product with 50% solid content was stored in a brown bottle. Proton NMR showed no anhydride present in the product.

Synthesis Example 15

42.6 g of Titanium (IV) isoproxide and 33.6 g of citraconic anhydride were mixed and heated at 55 C under nitrogen. The mixture was maintained at 55° C. for 1 hour. The viscous polymer product was obtained after evaporation of the diester side-product under vacuum.

Polymer Synthesis Example 16

9.7 g of isopropyl hexafluoroisopropanol methacrylate (MA-BTHB-OH), 5.9 g of 2-ethylhexyl methacrylate, 3.5 g of 2-hydroxyethyl methacrylate and 8.5 g of glycidyl methacrylate, were mixed in 120 g of THF solvent. The polymerization reaction took place in the presence of 1.0 g of AIBN at 75° C. under nitrogen for 20 hrs. After cooling down to room temperature, the reaction mixture was precipitated in DI water. The white polymer solid was washed and dried under vacuum at 45° C. with a yield of 27.2 g (99%). The Mw of the polymer measured by GPC was 19,100.

Polymer Synthesis Example 17

9.7 g of MA-BTHB-OH, 5.8 g of benzyl methacrylate, 5.1 g of 2-hydroxyethyl methacrylate and 6.4 g of glycidyl methacrylate, were mixed with in 120 g of tetrahydrofuran (THF) solvent. The polymerization reaction took place in the presence of 1.0 g of AIBN at 75° C. under nitrogen for 20 hrs. After cooling down to room temperature, the reaction mixture was precipitated in DI water. The white polymer solid was washed and dried under vacuum at 45° C. with a yield of 26.5 g (99%). The $M_w$ of polymer measured by GPC was 19,000.

Polymer Synthesis Example 18

15.0 g of MA-BTHB-OH, 6.0 g of styrene, 10.0 g of 2-hydroxypropyl methacrylate and 19.0 g of glycidyl methacrylate, were mixed in 200 g of Propylene glycol monomethyl ether acetate (PGMEA) solvent. The polymerization reaction took place in the presence of 0.97 g of AIBN at 75° C. under nitrogen for 24 h. After cooling down to room temperature, the reaction mixture was precipitated in DI water. The white polymer solid was washed and dried under vacuum at 45° C. with a yield of 50.0 g (>99%). The $M_w$ of polymer measured by GPC was 18,500.

Polymer Synthesis Example 19

18.5 g of MA-BTHB-OH and 12.3 g of glycidyl methacrylate, were mixed in 120 g of THF solvent. The polymerization reaction took place in the presence of 1.0 g of AIBN at 75° C. under nitrogen for 20 h. After cooling down to room temperature, the reaction mixture was precipitated in DI water. The white polymer solid was washed and dried under vacuum at 45° C. with a yield of 30.2 g (99%).

Polymer Synthesis Example 20

18.5 g of MA-BTHB-OH, 3.5 g of 2-hydroxyethyl methacrylate and 8.5 g of glycidyl methacrylate, were mixed in 120 g of THF solvent. The polymerization reaction was allowed in the presence of 1.0 g of AIBN at 75° C. under nitrogen for 20 hrs. After cooling down to room temperature, the reaction mixture was precipitated in DI water. The white polymer solid was washed and dried under vacuum at 45° C. with a yield of 29.8 g (99%).

Polymer Synthesis Example 21

10 g of butanetetracarboxylic acid dianhydride, 7 g of styrene glycol, 0.5 g of benzyltributylammonium chloride, and 35 g of propyleneglycol monomethyletheracetate (PGMEA) were charged into a flask with a condenser, thermal controller and a mechanical stirrer. Under nitrogen and stirring, the mixture was heated to 110° C. A clear solution was obtained after ~1-2 hr. The temperature was kept at 110° C. for 3 hrs. Upon cooling, 60 g of PGMEA and 36 g of propylene oxide were mixed with the above solution. The reaction was kept at 50° C. for 48 hrs. The reaction solution was cooled to room temperature and slowly poured into a large amount of water in a high speed blender. The polymer was collected and washed thoroughly with water. Finally the polymer was dried in a vacuum oven. 16 g of polymer was obtained with a $M_w$ measured by GPC of 20,000.

Synthesis Example 22

20.0 g of Hafnium isopropoxide, 80.0 g of acetic acid and 10.0 g of DI water were mixed by stirring in a flask under nitrogen for 10 minutes. The mixture was brought at 120° C. and held for about 2 hours. 10.0 g of DI water was then added. After 18 hrs of heating the reaction was allowed to cool. The reaction mix was evaporated to give a white dry mass (Hafnium oxide acetic acid, 9.93 g).

One gram of Hafnium oxide acetic acid, one gram of methacrylic acid and one gram of PGMEA were added to a vial, sonicated for 5 minutes and then heated to 130° C.

To 2 gram of this solution, 5 gram of 10% polymer solution made from Synthesis Example 17 in PGMEA/PGME 70:30 was added and diluted with 5 g of PGMEA/PGME 70:30. The mixture was filtered through 0.2 micron filter.

Composition Examples 1-10% wt/wt solutions of metal compound from Synthesis example 1-15 were prepared in PGMEA/PGME depending on the film thickness requirement. Some formulations contain 0.1-1% of gamma-valerolactone. After mixing, the solution was spin-coated on the silicon wafer and baked at 200-250° C. for between about 60 to about 120 seconds. The refractive index (n) and the extinction coefficient (k) values of the antireflective coating in the examples below were measured on a J. A. Woollam VASE32 ellipsometer. The formulation examples 1-15 and corresponding soluble, multi-ligand-substituted metal compound are listed in Table 1. The formulation generally contained 5.0% solid in total composition.

TABLE 1

| Formulation Examples using metal compound from Synthesis Examples above only | | | | |
|---|---|---|---|---|
| Formulation Examples | Synthesis Examples from above | Soft Bake Condition | Refractive Index, n 193 nm | Extinction Coefficient, k 193 nm |
| 1 | 1 | 225° C./60 s | 1.50 | 0.73 |
| 2 | 2 | 250° C./60 s | 1.65 | 0.40 |
| 3 | 3 | 225° C./60 s | 1.50 | 0.73 |
| 4 | 4 | 250° C./60 s | 1.63 | 0.40 |

TABLE 1-continued

Formulation Examples using metal compound from Synthesis Examples above only

| Formulation Examples | Synthesis Examples from above | Soft Bake Condition | Refractive Index, n 193 nm | Extinction Coefficient, k 193 nm |
|---|---|---|---|---|
| 5 | 5 | 200° C./60 s | 1.57 | 0.52 |
| 6 | 6 | 200° C./60 s | 1.57 | 0.52 |
| 7 | 7 | 225° C./60 s | 1.52 | 0.53 |
| 8 | 8 | 225° C./60 s | 1.54 | 0.47 |
| 9 | 9 | 250° C./60 s | 1.63 | 0.40 |
| 10 | 10 | 250° C./60 s | 1.56 | 0.69 |
| 11 | 11 | 225° C./60 s | 1.53 | 0.67 |
| 12 | 12 | 225° C./60 s | 1.54 | 0.49 |
| 13 | 13 | 225° C./60 s | 1.50 | 0.51 |
| 14 | 14 | 225° C./60 s | 1.56 | 0.48 |
| 15 | 15 | 225° C./60 s | 1.53 | 0.52 |

The formulation examples containing additional polymers are listed in Table 2.

TABLE 2

Formulation Examples containing additional polymers with the metal compound.

| Formulation Examples | Polymer Weight Ratio | Soft Bake Condition | Refractive Index n 193 nm | Extinction Coefficient k 193 nm |
|---|---|---|---|---|
| 16 | Example 8/Pxane* 95/5 | 225° C./60 s | 1.58 | 0.45 |
| 17 | Example 8/Pxane* 90/10 | 225° C./60 s | 1.61 | 0.39 |
| 18 | Example7/Polymer example16 95/5 | 240° C./60 s | 1.59 | 0.47 |
| 19 | Example8/Polymer example16 95/5 | 240° C./60 s | 1.58 | 0.48 |
| 20 | Example22/Polymer example17 30/70 | 250° C./60 s | 1.64 | 0.24 |
| 21 | In(AA)3**/example17 30/70 | 200° C./60 s | 1.79 | 0.25 |
| 22 | In(AA)3**/example19 50/50 | 200° C./60 s | 1.62 | 0.04 |

*Pxane is Pxane-1120, a polysiloxane product from SJPC.
**In(AA)3 is obtained from Aldrich.

Determination of M % in Cured Films

Metal % wt/wt in the metal oxide films were measured by elemental analysis and TGA weight loss measurement (Calcination). The results from two methods are consistent. The measure Metal % ranges from about 10 to about 70% at 200-250° C. for about 60 seconds film baking conditions depending on the composition in formulations.

Evaluation of Resistance to Solvents and Developer for Back Anti-Reflective Films PGMEA/PGME 70:30 solvent was dispensed on the silicon wafer coated with materials from formulation examples 1-22 at indicated temperatures in Table 1 and Table 2. Nitrogen blowing was used to remove the solvent after 60 seconds. No significant film losses were observed. In most cases, a 20° C. to 40° C. lower baking temperature can still pass (no loss of film thickness) the soaking test in PGMEA/PGME 70:30 solvent. Similar experiments were performed with developer 2.38% wt/wt TMAH. The films from Table 1 and Table 2 showed good resistance to developer (no loss of film thickness). Partial film loss in developer can be achieved by lowering baking temperature if desired.

Formulation Moisture Sensitivity Tests

The solutions of Formulation Examples 6, 7, 8, 10, 11 were exposed to air (bottle open) for 0.5 h, 1 h, 5 h, 8 h, 10 h, 14 h, 16 h, 20 h and 24 h (h=hour). After closing the bottles, the samples are subjected to long term stability test by coating the solution periodically e.g. 1 wk, 1 month, etc. and examining the coating quality/soaking test performances. The formulation was spin coated on a silicon wafer and baked at 200-250° C./60 s as described above. The films of the examples demonstrated good coating quality (no particles/voids) even after 8 h to 24 h exposure to air and for at least 1 week. The reference material (Ti(IV)BTP, Aldrich) was not stable for 1 week after about 1 h air exposure and particles were observed on the coating after this time.

Shelf-Life Studies on LPC Particle Size Measurement and Defect Evaluations

Liquid particle count (LPC) and coating defects aging shelf life studies were performed on formulation example 10 at 25° C./initial, 25° C. for 2 weeks, 25° C. for 3 weeks followed by −20° C. for 1 week, 25° C. for 3 weeks followed by 40° C. for 1 week as shown in Table 3.

Formulation Example 10 was spin coated onto Si wafers. The wafers were inspected by a Zeiss Axiotion II Inspection Microscope (Confocal Scan) or by a SEMVision CX Inspection Microscope from Applied Materials. Defect inspection/analysis was done on a KLA 2360 wafer inspection system or a Surfscan 6220 wafer surface analysis system.

No significant change was observed initially and after aging the formulations, thus the materials were acceptably stable.

TABLE 3

LPC and defect data of Formulation and Coating Example 10

| | Initial | 2 weeks 25° C. | 3 weeks 25° C. | 3 weeks 25° C./ 1 week −20° C. | 3 weeks 25° C./ 1 week 40° C. |
|---|---|---|---|---|---|
| LPC@0.15 μm (#/ml) | 13.9 | 5.7 | — | 3.0 | 18.6 |
| LPC@0.18 μm (#/ml) | 10.1 | 3.9 | — | 1.7 | 15.4 |
| LPC@0.20 μm (#/ml) | 8.0 | 2.8 | — | 1.3 | 13.3 |
| LPC@0.30 μm (#/ml) | 2.8 | 0.6 | — | 0.1 | 6.9 |
| LPC@0.50 μm (#/ml) | 1.0 | 0.1 | — | 0 | 3.6 |
| KLA Defects@0.20 (#/cm$^2$) | — | — | 0.44 | 0.16 | 0.79 |
| KLA Defects@0.25 (#/cm$^2$) | — | — | 0.12 | 0.07 | 0.36 |
| Surfscan (#/cm2) | — | — | 0.04 | 0.04 | 0.16 |

Wet Etch-Rate Tests

Formulation Example 8 was tested using the stripping recipes listed in Table 4. The initial thickness of the film was 35 nm. The stripping time as recorded after the film was washed away was determined visually or by measuring film thickness before and after soaking. All the films were successfully removed after stripping test.

TABLE 4

Stripping test results of metal oxide film under various conditions.

| Stripping Solution | Stripping Condition |
|---|---|
| 85% Phosphoric Acid | 2 min @ 70° C. |
| 3% Hydrofluoric Acid | 1 min @ 25° C. |
| 10% TMAH | 1 min @ 60° C. |
| 10% Hydrogen Peroxide | 1 min @ 50° C. |
| NH$_4$OH/H$_2$O$_2$/H$_2$O 1/4/40 | 30 sec @ 28° C. |

Lithographic Evaluation Example 1

The performance of the Ti metallic anti-reflective coating formulation was evaluated using AZ® 2110P photoresist (product of AZ Electronic Materials USA Corp., Somerville, N.J.). A silicon wafer was coated with Formulation Example 8 and baked at 225° C. for 60 seconds to form a 43 nm thick film. Then using AZ® EXP AX2110P photoresist film targeting at 190 nm was coated on top and baked at 100° C. for 60 seconds. The wafer was then imaged using a 193 nm Nikon 306D exposure tool with a Numerical Aperture (NA) of 0.85, with Y-Dipole Illumination with a 0.85 outer sigma, and 0.55 inner sigma. The exposed wafer was then baked at 110° C. for 60 seconds and developed using AZ® 300MIF developer (TMAH) for 30 seconds. The top down and cross-section patterns when observed under scanning electron microscope showed no significant collapse in the process window. Good pattern profile was observed at Line/Space 80 nm 1:1 with photospeed of 26 mJ/cm2.

Lithography Evaluation Example 2

The performance of the Ti metallic anti-reflective coating formulation was evaluated using AZ® 2110P photoresist (product of AZ Electronic Materials USA Corp., Somerville, N.J.). A silicon wafer was coated with Formulation and Coating Example 18 and baked at 225° C. for 60 seconds to form a 41 nm thick film. Then using AZ® EXP AX2110P photoresist film targeting at 190 nm was coated on top and baked at 100° C. for 60 seconds. The wafers were then imaged using a 193 nm Nikon 306D exposure tool with a Numerical Aperture (NA) of 0.85, with Y-Dipole Illumination with an 0.85 outer sigma, and 0.55 inner sigma. The exposed wafers were then baked at 110° C. for 60 seconds and developed using AZ® 300MIF developer (TMAH) for 30 seconds. The top down patterns when observed under scanning electron microscope showed no significant collapse. Good pattern profile via cross-section scanning electron microscope was observed at L/S 80 nm 1:1 with photospeed of 26 mJ/cm2.

Lithography Evaluation Example 3

The performance of the Ti metallic anti-reflective coating formulation was evaluated for trilayer scheme in immersion lithography. A silicon wafer was coated with AZ® ArFU98-150 (available from AZ Electronic Materials, 70, Meister Ave. Somerville N.J.) carbon underlayer with a film thickness of 150 nm bake at 250° C. for 60 seconds. Formulation and Coating Example 9 was coated and baked at 250° C. for 60 seconds to form a 25 nm thick film on the carbon underlayer. Then using immersion photoresist film targeting at 120 nm was coated on top and baked at 120° C. for 60 seconds. The wafers were then imaged using a 193 nm immersion exposure tool of dipole40Y with 0.979/0.824 X polarization and a Numerical Aperture (NA) of 1.2. The exposed wafers were then baked at 110° C. for 60 seconds and developed using AZ® 300MIF developer (TMAH) for 30 seconds. The top down patterns when observed under scanning electron microscope showed no significant collapse. Good pattern profile via cross-section scanning electron microscope was observed at L/S 45 nm 1:1 with photospeed of 33 mJ/cm2.

Lithography Evaluation Example 4

EUV exposure was performed using excimer micro-exposure tool (eMET) at SEMATECH at the University of Albany or micro-exposure tool (MET) at Lawrence Berkeley National Laboratory (LBNL). EUV photoresist was coated on top of above underlayer. It was baked and exposed with 0.3 numerical aperture (NA) with quadrupole or annular illuminations. The MET tool provided a 5× reduction, a 200×600 um field on wafer plane. After development, the litho performance was evaluated with both CDSEM topdown measurements and cross section pictures taken under an SEM instrument. A silicon wafer was coated with Formulation and Coating Example 12 and baked at 225° C. for 60 seconds to form a 25 nm thick film. Then the EUV photoresist was coated to give a film of 190 nm. The photoresist was then exposed by EUV radiation. The exposed wafers were then baked and developed. The top down patterns when observed under scanning electron microscope showed no significant collapse. Good pattern profile via cross-section scanning electron microscope was observed at L/S 30 nm 1:1 with photospeed of 12.6 mJ/cm$^2$.

We claim:
1. A soluble, multi-ligand-substituted metal compound of the following structure:

wherein n is about 1 to about 20, $R_1$ is independently selected from a group consisting of $C_1$-$C_6$ unsubstituted alkyl, $C_1$-$C_6$ substituted alkyl and $R_2$, $R_2$ is independently selected from a group consisting of $C_6$-$C_{20}$ unsubstituted alkyl, $C_6$-$C_{20}$ substituted alkyl, a —COR$_3$ group, a —N(R$_3$)$_2$ group, —SO$_2$R$_3$ group, a —SOR$_3$ group and a —SR$_3$ group, wherein each R$_3$ is independently selected from a group consisting of unsubstituted aromatic, substituted aromatic, unsubstituted heteroaromatic, substituted heteroaromatic group, $C_1$-$C_{20}$ unsubstituted alkyl, $C_1$-$C_{20}$ substituted alkyl, $C_1$-$C_{20}$ unsubstituted alkenyl, $C_1$-$C_{20}$ substituted alkenyl group, functionalized alkylene with a structure of -alkylene-COOR$_3$', wherein R$_3$' is independently selected from a group consisting of $C_1$-$C_6$ substituted alkyl and $C_1$-$C_6$ substituted alkyl.

2. The compound of claim 1, wherein the metal is titanium, zirconium, tantalum, lead, antimony, thallium, indium, ytterbium, gallium, hafnium, aluminum, magnesium, molybdenum, germanium, tin, iron, cobalt, nickel, copper, zinc, gold, silver, cadmium, tungsten, or platinum.

3. The compound of claim 2, wherein at least one of $R_1$, $R_2$, $R_3$ or $R_3'$ is a partially of fully fluorinated alkyl group.

4. The compound of claim 2, wherein at least one $R_2$ is selected from a group consisting of alkyl, aromatic ester and heteroaromatic ester.

5. The compound of claim 2, wherein the metal is more than one metal when n is about 2 to about 20.

6. The compound of claim 2, wherein n is 2 to 20.

7. The compound of claim 2, wherein n is 1.

8. A composition comprising:
   a. A soluble, multi-ligand-substituted metal compound of the following structure:

wherein n is about 1 to about 20, $R_1$ is independently selected from a group consisting of $C_1$-$C_6$ unsubstituted alkyl, $C_1$-$C_6$ substituted alkyl and $R_2$, $R_2$ is independently selected from a group consisting of $C_6$-$C_{20}$ unsubstituted alkyl, $C_6$-$C_{20}$ substituted alkyl, a —$COR_3$ group, a —$N(R_3)_2$ group, —$SO_2R_3$ group, a —$SOR_3$ group and a —$SR_3$ group, wherein each $R_3$ is independently selected from a group consisting of unsubstituted aromatic, substituted aromatic, unsubstituted heteroaromatic, substituted heteroaromatic group, $C_1$-$C_{20}$ unsubstituted alkyl, $C_1$-$C_{20}$ substituted alkyl, $C_1$-$C_{20}$ unsubstituted alkenyl, $C_1$-$C_{20}$ substituted alkenyl group, functionalized alkylene with a structure of -alkylene-$COOR_3'$, wherein $R_3'$ is independently selected from a group consisting of $C_1$-$C_6$ substituted alkyl and $C_1$-$C_6$ substituted alkyl; and,
   b. a solvent.

9. The composition of claim 8 where the composition further comprises an organic or silicon based crosslinkable polymer.

10. The composition of claim 8, further comprising at least one of a thermal acid generator, a thermal base generator, or a thermally activated peroxide.

11. The composition of claim 8, wherein the metal is titanium, zirconium, tantalum, lead, antimony, thallium, indium, ytterbium, gallium, hafnium, aluminum, molybdenum, magnesium, germanium, tin, iron, cobalt, nickel, copper, zinc, gold, silver, cadmium, tungsten, or platinum.

12. The composition of claim 8, wherein at least one of $R_1$, $R_2$, $R_3$ or $R_3'$ is a partially or fully fluorinated alkyl group.

13. The composition of claim 8, wherein at least one $R_2$ is selected from a group consisting of alkyl, alkenyl, aromatic ester and heteroaromatic ester.

14. The composition of claim 8, wherein the metal is more than one metal when n is about 2 to about 20.

15. The composition of claim 8, wherein n is 2 to 20.

16. The composition of claim 8, wherein n is 1.

17. The composition of claim 15, further comprising a crosslinking additive.

18. A method of manufacturing an electronic device comprising:
   a. applying a composition from claim 8 onto a substrate to form a film; and,
   b. baking the film.

19. The method of claim 18, further comprising removing the composition using a stripper composition.

20. The method of claim 19, wherein the stripper is selected from a group consisting of acid, base, peroxide, and mixtures thereof.

21. A composition comprising:
   a. A soluble, multi-ligand-substituted metal compound of the following structure:

wherein n is about 1 to about 20, $R_1$ is independently selected from a group consisting of $C_1$-$C_6$ unsubstituted alkyl, $C_1$-$C_6$ substituted alkyl and $R_2$, $R_2$ is independently selected from a group consisting of unsubstituted aromatic, substituted aromatic, unsubstituted heteroaromatic, substituted heteroaromatic group, $C_6$-$C_{20}$ unsubstituted alkyl, $C_6$-$C_{20}$ substituted alkyl, $C_6$-$C_{20}$ unsubstituted alkenyl, $C_6$-$C_{20}$ substituted alkenyl group, a —$COR_3$ group, a —$N(R_3)_2$ group, —$SO_2R_3$ group, a —$SOR_3$ group and a —$SR_3$ group, wherein each $R_3$ is independently selected from a group consisting of unsubstituted aromatic, substituted aromatic, unsubstituted heteroaromatic, substituted heteroaromatic group, $C_1$-$C_{20}$ unsubstituted alkyl, $C_1$-$C_{20}$ substituted alkyl, $C_1$-$C_{20}$ unsubstituted alkenyl, $C_1$-$C_{20}$ substituted alkenyl group, functionalized alkylene with a structure of -alkylene-$COOR_3'$, wherein $R_3'$ is independently selected from a group consisting of $C_1$-$C_6$ substituted alkyl and $C_1$-$C_6$ substituted alkyl;
   b. a solvent; and
   c. an organic or silicon based crosslinkable polymer.

22. A composition comprising:
   a. A soluble, multi-ligand-substituted metal compound of the following structure:

wherein n is about 1 to about 20, $R_1$ is independently selected from a group consisting of $C_1$-$C_6$ unsubstituted alkyl, $C_1$-$C_6$ substituted alkyl and $R_2$, $R_2$ is independently selected from a group consisting of unsubstituted aromatic, substituted aromatic, unsubstituted heteroaromatic, substituted heteroaromatic group, $C_6$-$C_{20}$ unsubstituted alkyl, $C_6$-$C_{20}$ substituted alkyl, $C_6$-$C_{20}$ unsubstituted alkenyl, $C_6$-$C_{20}$ substituted alkenyl group, a —$COR_3$ group, a —$N(R_3)_2$ group, —$SO_2R_3$ group, a —SORB group and a —$SR_3$ group, wherein each $R_3$ is independently selected from a group consisting of unsubstituted aromatic, substituted aromatic, unsubstituted heteroaromatic, substituted heteroaromatic group, $C_1$-$C_{20}$ unsubstituted alkyl, $C_1$-$C_{20}$ substituted alkyl, $C_1$-$C_{20}$ unsubstituted alkenyl, $C_1$-$C_{20}$ substituted alkenyl group, functionalized alkylene with a structure of -alkylene-COOR$_3$', wherein R$_3$' is independently selected from a group consisting of $C_1$-$C_6$ substituted alkyl and $C_1$-$C_6$ substituted alkyl;

b. a solvent; and c. at least one of a thermal acid generator, a thermal base generator, or a thermally activated peroxide.

* * * * *